US011285206B2

(12) United States Patent
Wen et al.

(10) Patent No.: US 11,285,206 B2
(45) Date of Patent: Mar. 29, 2022

(54) HEAT-RESISTANT RECOMBINANT NEWCASTLE DISEASE VIRUS VACCINE STRAIN CAPABLE OF EXPRESSING TRUNCATED FIBER 2 PROTEIN OF FOWL ADENOVIRUS SEROTYPE 4, PREPARATION METHOD AND APPLICATION THEREOF

(71) Applicant: INSTITUTE OF ANIMAL HUSBANDRY AND VETERINARY SCIENCES, HUBEI ACADEMY OF AGRICULTURAL SCIENCES, Wuhan (CN)

(72) Inventors: Guoyuan Wen, Wuhan (CN); Li Li, Wuhan (CN); Yu Shang, Wuhan (CN); Huabin Shao, Wuhan (CN); Qingping Luo, Wuhan (CN); Honglin Wang, Wuhan (CN); Ling Luo, Wuhan (CN); Rongrong Zhang, Wuhan (CN); Hongcai Wang, Wuhan (CN); Tengfei Zhang, Wuhan (CN); Wenting Zhang, Wuhan (CN); Qin Lu, Wuhan (CN)

(73) Assignee: INSTITUTE OF ANIMAL HUSBANDRY AND VETERINARY SCIENCES, HUBEI ACADEMY OF AGRICULTURAL SCIENCES, Wuhan (CN)

( * ) Notice: Subject to any disclaimer, the term of this patent is extended or adjusted under 35 U.S.C. 154(b) by 0 days.

(21) Appl. No.: 17/234,795

(22) Filed: Apr. 20, 2021

(65) Prior Publication Data

US 2022/0054626 A1 Feb. 24, 2022

(30) Foreign Application Priority Data

Aug. 19, 2020 (CN) .......................... 202010839278.3

(51) Int. Cl.
| | | |
|---|---|---|
| *C12N 7/00* | (2006.01) | |
| *A61K 39/17* | (2006.01) | |
| *A61K 35/763* | (2015.01) | |

(52) U.S. Cl.
CPC ................. *A61K 39/17* (2013.01); *C12N 7/00* (2013.01); *C12N 2760/18021* (2013.01); *C12N 2760/18034* (2013.01); *C12N 2760/18052* (2013.01)

(58) Field of Classification Search
CPC .............. A61K 39/17; A61K 2039/552; A61K 39/155; C12N 2760/18021; C12N 2760/18034; C12N 2760/18052; C12N 2760/18122; C12N 15/86; C12N 2760/18144; A61P 31/14
See application file for complete search history.

(56) References Cited

FOREIGN PATENT DOCUMENTS

| CN | 105420261 A | 3/2016 |
| CN | 105969740 A | 9/2016 |

OTHER PUBLICATIONS

Kai-Yue Tian et al, "Construction And Identification Of Recombinant Newcastle Disease Virus Expressing The Fiber2 Gene Of Fowl Adenovirus Serotype 4 Chinese Epidemic Strain", Sep. 2019, pp. 1697-1702, vol. 39, No. 9, Chinese Journal of Veterinary Medicine.

*Primary Examiner* — Bao Q Li

(57) ABSTRACT

A heat-resistant recombinant Newcastle Disease Virus vaccine strain rLS-tFib2-C capable of expressing truncated Fiber 2 protein of fowl adenovirus serotype 4 has been preserved at the China Center for Type Culture Collection, Wuhan University, Wuhan, China with the preservation number of CCTCC No. V202042.

4 Claims, 2 Drawing Sheets

Specification includes a Sequence Listing.

HEAT-RESISTANT RECOMBINANT NEWCASTLE DISEASE VIRUS VACCINE STRAIN CAPABLE OF EXPRESSING TRUNCATED FIBER 2 PROTEIN OF FOWL ADENOVIRUS SEROTYPE 4, PREPARATION METHOD AND APPLICATION THEREOF

TECHNICAL FIELD

The present disclosure relates generally to molecular biology technology and microbiology, and in particular relates to a heat-resistant recombinant Newcastle Disease Virus (NDV) vaccine strain capable of expressing truncated Fiber 2 protein of Fowl Adenovirus serotype 4.

More specifically, the present disclosure also relates to a reverse genetic manipulation technology used to transform the NDV LaSota vaccine strain by HN gene replacement and truncated Fiber 2 gene insertion to obtain a new recombinant NDV vaccine strain rLS-tFib2-C, and application of the strain in preparation of heat-resistant live vaccine against Angraradisease and Newcastle disease.

BACKGROUND

Fowl Adenovirus (FAdV) is a worldwide infectious disease pathogen that frequently occurs in poultry and wild birds. FAdV is a member of the avian adenovirus genus of the adenovirus family. The viruses of this genus can be divided into three groups, namely group I, group II and group III. The relationship between group II, group III FAdV and disease is relatively clear, while group I FAdV has the most types of strains and the most complicated relationship with disease, and there are as many as 12 serotypes of group I FAdV. Fowl Adenovirus serotype 4 (FAdV-4) is one of the representative strains of FAdV in group I. The virus mainly causes Angraradisease, also known as hydropericardial-hepatitis syndrome. The disease was first discovered in the Ankara region of Pakistan, so it is called Angraradisease, and its fatality rate can reach 30%-70%. Since 2015, Angraradisease has spread and broke out in Henan, Anhui, Shandong and other places, causing huge economic losses to the poultry industry in China. At present, there is no vaccine against Angraradisease on the market, which has caused great difficulties in prevention and control of the disease. The development of a safe and efficient Fowl Adenovirus vaccine is an important means to control the virus epidemic.

FAdV is a double-stranded DNA virus with a molecular diameter of about 70-90 nm, no envelope structure, and with an icosahedral symmetric structure. The capsid protein of the virus is mainly composed of Hexon, Penton and Fiber. Fiber and Penton are respectively responsible for the two processes of virus adsorption and invasion during the virus infection cycle. Fiber protein has two independent Fiber encoding genes named Fiber1 and Fiber2. Penton and Fiber2 are antigenic and can induce virus neutralizing antibodies.

Newcastle Disease (ND) is an acute, highly lethal and highly infectious disease in chickens caused by Newcastle Disease Virus (NDV). The epidemic of ND has caused huge economic losses to the poultry industry and is listed as one of the two A poultry infectious diseases by the International Veterinary Administration. NDV has only one serotype, but the virulence of different strains is quite different. According to the virulence, the Newcastle disease virus can be divided into virulent strains, medium virulence and weak virulent strains.

In China, Newcastle disease is one of the animal diseases subject to national compulsory immunization. Newcastle disease vaccines are divided into two categories: live vaccines and inactivated vaccines. Live vaccines include lineage I vaccines (Mukteswar strain), lineage II vaccines (HB1), lineage III vaccines (F strain), lineage IV vaccines (LaSota strain), Clone-30 and V4 strain. Among them, lineage I vaccines are medium-virulence live vaccines, and the others are attenuated live vaccines. The inactivated vaccine is mostly an oil emulsion vaccine prepared by lineage IV vaccines or clone 30 after inactivation. LaSota strain vaccine is very popular among farmers for its low virulence, good immunogenicity and high immune protection rate. However, the LaSota strain virus has poor thermal stability, and the live vaccine prepared therefrom has high requirements on the cold chain, which is not conducive to the promotion and application in tropical and remote areas.

With the continuous advancement of reverse genetic manipulation technology, new multiple live vaccine based on NDV vectors have become a hot spot for new vaccine research and development. Many pathogenic immunogenic genes have been successfully expressed in NDV vectors, and have achieved better immune protection effects, such as VP2 protein of infectious bursal disease virus and HA protein of H5 subtype avian influenza virus. Such vaccines take advantages of inducing systemic immunity, high growth characteristics of chicken embryos, low production costs, and simple immunization methods.

However, most of current research reports are solely on the Angraradisease vaccine or Newcastle disease vaccine, and there is no research report on the dual live vaccine. Therefore, in view of the two important diseases of Angraradisease and Newcastle Disease, which seriously endanger China's poultry industry, there is an urgent need to develop a new dual live vaccine that is safe, efficient, stable, and simple in immunization.

DESCRIPTION OF DRAWINGS

FIG. 1 shows the construction strategy of the heat-resistant recombinant NDV vaccine strain.

FIG. 2 shows a schematic diagram of the immunogenic gene of Fowl Adenovirus serotype 4 expressed by a recombinant NDV vector.

DETAILED DESCRIPTION

Figure 3:
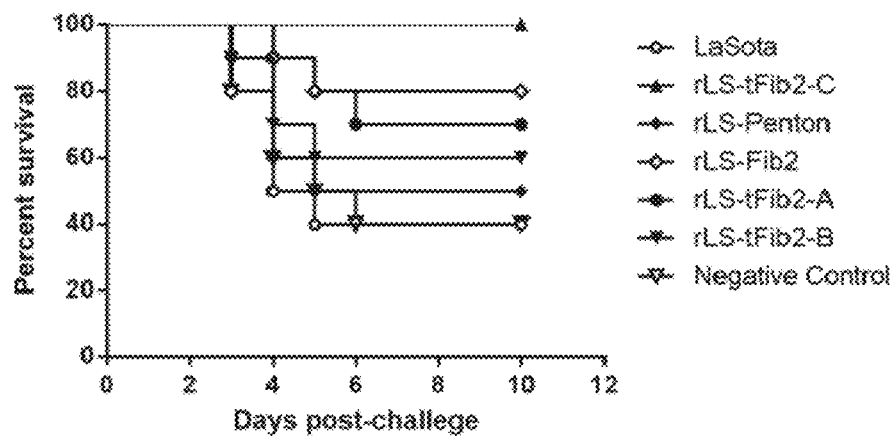
FIG. 3 shows the survival curve of Fowl Adenovirus attack of test chicken immunized with recombinant NDV.

The present disclosure will be further described below with reference to the figures and examples, but the content of the present disclosure is not limited to the following examples.

Example 1

Figures 1, 2:
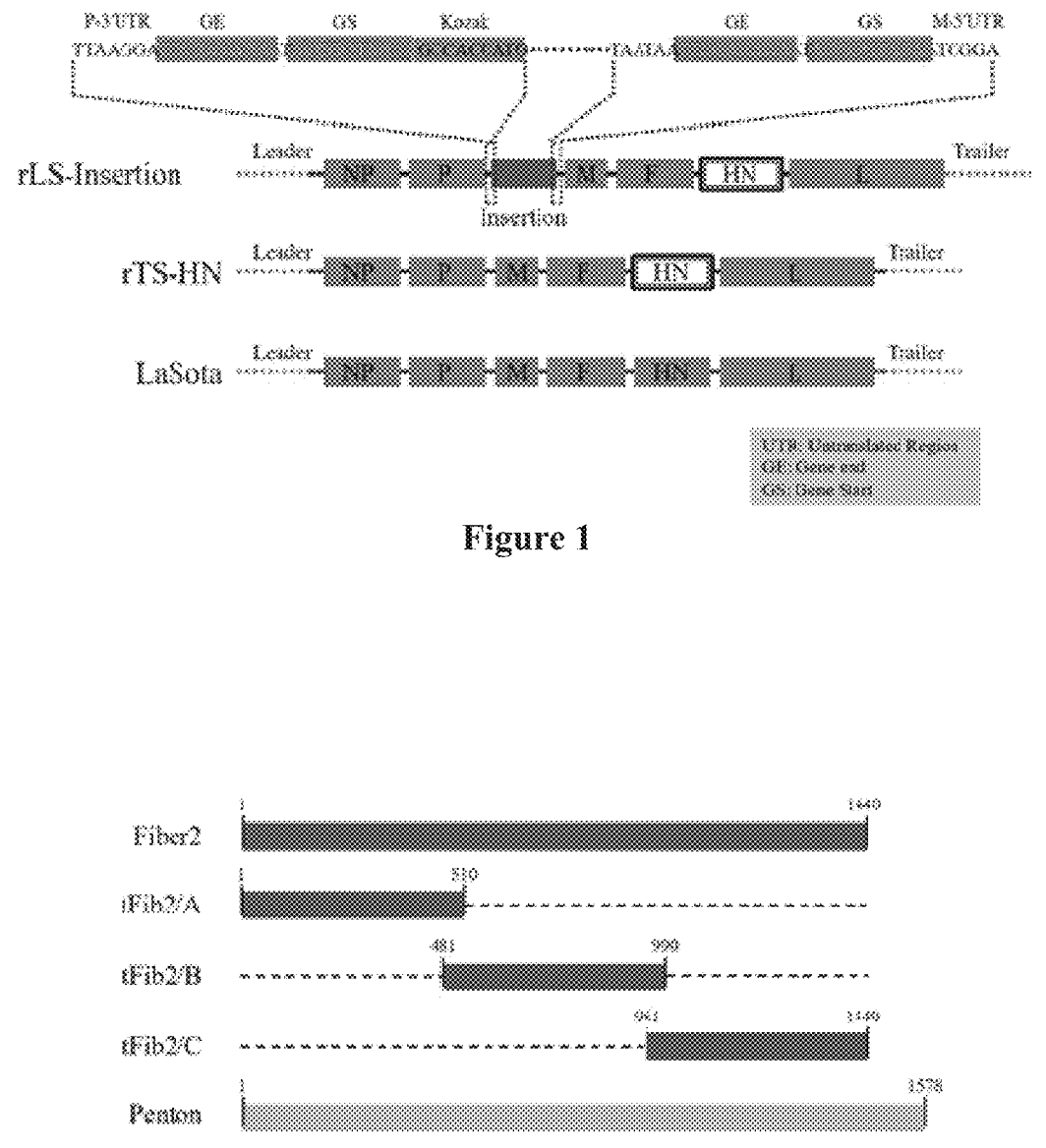

Construction and Rescue of a Heat-Resistant Recombinant NDV Strain Capable of Expressing Fowl Adenovirus Serotype 4 Immunogenic Genes A transcription plasmid of NDV LaSota strain was used as a template and reverse genetic manipulation technology was employed. Firstly an HN gene thereof was replaced with an HN gene of a heat-resistant NDV TS09-C strain, and then five Fowl Adenovirus serotype 4 immunogenic genes (complete Fiber2, three truncated Fiber2 and complete Penton) were inserted between the P and M genes of the LaSota strain genome. The specific modification strategy was shown in FIG. 1, and the sequence positions of the five inserted genes were shown in FIG. 2. The modified transcription plasmid and three helper plasmids co-transfected BHK-21 cells to obtain five recombinant NDV strains, namely rLS-Penton, rLS-Fib2, rLS-tFib2-A, rLS-tFib2-B and rLS-tFib2-C. In the above-mentioned five recombinant virus construction and rescue schemes, the remaining operations are basically the same except for the differences in the primers used to amplify the immunogenic genes of Fowl Adenovirus.

The HN protein gene of the LaSota strain has the sequence of SEQ ID NO: 1.

1.1 HN Gene Replacement of the Transcription Plasmid of the NDV

Using a cDNA cloning plasmid of the NDV LaSota strain as a template, fragments other than HN gene were amplified by PCR. The forward primer has the sequence of SEQ ID NO: 3, and the reverse primer has the sequence of SEQ ID NO: 4. The cDNA template was digested with nuclease DpnI, and a target fragment 1 was recovered by agarose gel electrophoresis.

The HN gene is amplified by PCR using the cDNA of the heat-resistant TS09-C strain of NDV as a template. The forward primer has the sequence of SEQ ID NO: 5, and the reverse primer has the sequence of SEQ ID NO: 6. A target fragment 2 was recovered by Agarose gel electrophoresis.

The target fragment 1 and target fragment 2 were connected by In-fusion in vitro ligation kit. The ligation product was transformed into *E. coli* DH5a cell. The transformed product was coated with LB medium, and single colony was selected and cultured in liquid medium. The HN gene was amplified by PCR for identification positive plasmid, and the positive plasmid was extracted for sequencing analysis of the whole plasmid. The plasmid with correct sequencing was named pTS-HN.

1.2 Insertion of Fowl Adenovirus Serotype 4 Immunogenic Gene to Transcription Plasmid of NDV Using the recombinant NDV plasmid pTS-HN as the template and the P and M intergenic regions as the starting point, the full length of the cDNA cloned plasmid of the rTS-HN strain was amplified by PCR. The forward primer has the sequence of SEQ ID NO: 7, and the reverse primer has the sequence of SEQ ID NO: 8. After the amplification was completed, the plasmid template was digested with nuclease DpnI, and a target fragment 3 was recovered by Agarose gel electrophoresis.

Using the genomic DNA of the FAdV-4 HB1510 isolate as a template, a fragment of the region 961-1440 of the Fiber 2 gene (tFib2/C) is amplified by PCR. The forward primer has the sequence of SEQ ID NO: 9, and the reverse primer has the sequence of SEQ ID NO: 10. A target fragment 4 was recovered by agarose gel electrophoresis. The primers were added with the gene start motif, gene stop motif, translation Kozak motif, start codon and stop codon of NDV.

The region 961-1440 of the Fiber 2 gene (Fiber2/C gene) of the Fowl Adenovirus serotype 4 has the sequence of SEQ ID NO: 2.

The target fragment 3 and target fragment 4 were connected by in-fusion in vitro ligation kit. The ligation product was transformed into *E. coli* DH5a cells. The transformed product was coated with LB medium, and single colony was selected and cultured in liquid medium. The truncated Fiber 2 gene was amplified by PCR for identifying the positive plasmid, and the positive plasmid was extracted for sequencing analysis of the whole plasmids. The plasmid with correct sequencing was named pLS-tFib2-C.

1.3 Rescue and Recovery of Recombinant NDV

When BHK-21 cells grow to 80-90% density, inoculated with recombinant vaccinia virus expressing T7 RNA polymerase (0.01 MOI). After 1 hour, the transcription plasmid pLS-tFib2-C and three helper plasmids (pVAX-NP, pVAX-P and pcDNA-L) were co-transfected into BHK-21 cells. 96-120 hours after transfection, the culture supernatant was collected and the culture supernatant was filtered with a 0.22 μm filter. The culture supernatant was inoculated into SPF chicken embryos aged 9-10 days, cultured for 96-120 h, and chicken embryo allantoic fluid was collected. Through HA titer determination and RT-PCR sequencing analysis, the recombinant NDV strain rLS-tFib2-C was obtained. The construction methods and steps of the remaining four recombinant NDV strains were basically the same as this strain, and finally five recombinant NDV strains were obtained.

Example 2

Immunogenicity Test of Heat-Resistant Recombinant NDV Strain Capable of Expressing Fowl Adenovirus Serotype 4a Immunogenic Gene The immune protection test against Fowl Adenovirus for the five above-mentioned recombinant NDV strains were carried out. Seventy one-week-old SPF chicks were randomly divided into 7 groups, 10 per group. Groups 1-5 were immunized with recombinant NDV strains rLS-Fib2, rLS-tFib2-A, rLS-tFib2-B, rLS-tFib2-C, rLS-Penton, respectively. Group 6 was immunized with LaSota strain, and group 7 was a blank control group. The immunization dose was $10^7$ EID$_{50}$/bird, and the immunization method was nose drops and eye drops. Two weeks after the initial immunization, a booster immunization was carried out in the same manner and dose. Two weeks after immunization, 7 groups of test chickens were challenged with Fowl Adenovirus serotype 4 virulent at a dose of 10 LD$_{50}$/bird. After that, the health status of the chickens was observed every day, the death situation was recorded, and the survival curve of the test chickens was drawn. As shown in FIG. 3, the survival rates of rLS-Fib2, rLS-tFib2-A, rLS-tFib2-B, rLS-tFib2-C, rLS-Penton, LaSota and the blank control group were 80%, 70%, 60%, 100%, 50%, 40% and 40%, respectively. Therefore, among the five newly constructed recombinant NDV, only rLS-tFib2-C strain can provide 100% protection for immunized chickens against Fowl Adenovirus serotype 4. The rLS-tFib2-C strain also had a 100% protection against NDV. Therefore, the rLS-tFib2-C strain can be used as a candidate strain for the dual heat-resistant live vaccine against Angraradisease and Newcastle disease.

Example 3

Thermal Stability Test of Recombinant NDV Strain rLS-tFib2-C

The allantoic fluid infected with the recombinant NDV rLS-tFib2-C strain was aliquoted in EP tubes with 100 μL/tube, and heat-treated in a 56° C. water bath. The LaSota strain control was set. The virus allantoic fluid was taken out at 0, 2, 5, 10, 15, 30, 60, 120, and 180 minutes, and quickly placed on ice to detect the HA titer of the virus and the changes in titer is counted. The results showed that the rLS-tFib2-C strain still had hemagglutination titer after heat treatment for 120 minutes, while the control LaSota strain had dropped to 1 log 2 after heat treatment for 5 minutes and to 0 for 10 minutes. The heat resistance of virus infectivity was further tested. After the corresponding time of treatment at 56° C., the BHK-21 cells were inoculated with a gradient dilution and the TCID$_{50}$ titer change was measured. The curve of the heat resistance of infectivity was drawn. The time $T_{90}$ was calculated required for the infectivity to decrease by 1 $\log_{10}$ (90%). The results showed that the $T_{90}$ of rLS-tFib2-C strain and LaSota strain were 12.4 and 1.5 min, respectively. Therefore, compared with the parent strain LaSota, the thermal stability of the recombinant NDV rLS-tFib2-C strain has been significantly improved.

Example 4

Cell Proliferation Test of Recombinant NDV Strain rLS-tFib2-C

Figure 4:
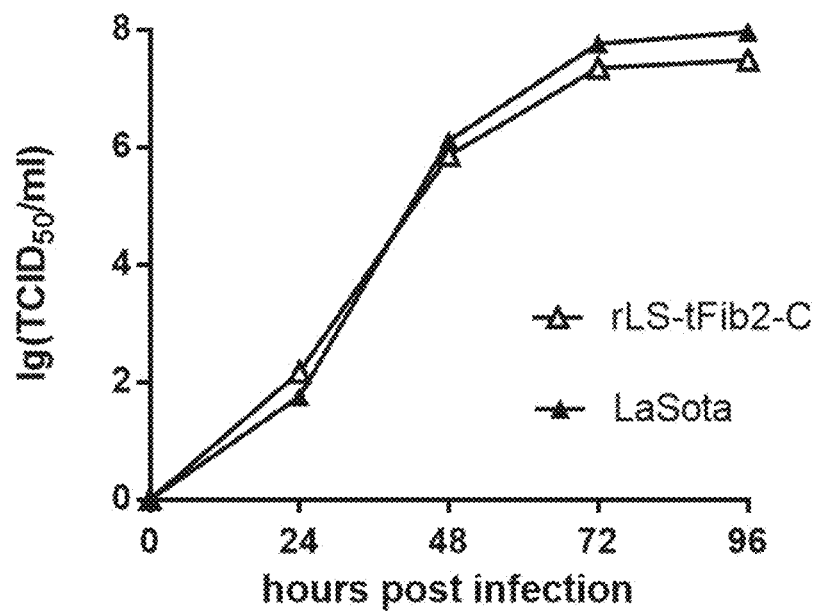
FIG. 4 shows the growth curve of recombinant NDV

In order to analyze whether HN gene replacement and Fiber2/C gene insertion affect the cell proliferation titer of rLS-tFib2-C strain, the cell proliferation of rLS-tFib2-C and the parent LaSota strain were compared. The two diluted viruses were inoculated into BHK-21 cells that had grown into a dense monolayer, and cell supernatants were collected at 6, 12, 24, 48, 72, and 96 hours after inoculation. The collected supernatant was diluted by a 10-fold gradient, and 100 μL of each dilution was inoculated into a 96-well plate containing a single layer of BHK-21 cells. Three replicates were set for each dilution. $TCID_{50}$ was calculated according to the cytopathic condition and the growth kinetic curve of the virus was drawn. The results were shown in FIG. 4. The rLS-tFib2-C strain basically reached a plateau 72 h after infection with the cells, with a titer of $10^{7.50}$ $TCID_{50}$/ml, which was similar to the growth curve of the parent LaSota strain. Therefore, the genetic modification of the virus did not affect the cell proliferation titer of the rLS-tFib2-C strain.

Example 5

Pathogenicity Test of Recombinant NDV Strain rLS-tFib2-C

The pathogenicity of rLS-tFib2-C strain is evaluated by the mean death time of minimum lethal dose of chicken embryo of the virus (MDT/MLD) and the intracerebral pathogenicity index (ICPI). The detection method for MDT/MLD was as follows: the allantoic fluid of the rLS-tFib2-C strain was 10-fold serial diluted and inoculated into SPF chicken embryos with 100 μL/piece. Observation was continued for 7 days, the death time of the chicken embryos was recorded, and the MDT/MLD value was calculated. The detection method for ICPI was as follows: the allantoic fluid of the rLS-tFib2-C strain with 10-fold dilutions was inoculated into 1-day-old SPF chicks with 10 per group. The inoculation volume was 50 μL/bird. Observe once a day, and score the chickens. Normal chickens were scored 0, sick chicken was scored 1, and dead chicken was scored 2. The ICPI value was calculated with a total of 8 days of observation. The results showed that the chicken embryos inoculated with different dilutions of the virus did not die for 120 h. The MDT/MLD value of the rLS-tFib2-C strain was greater than 120 h, and the ICPI value was 0.00. Similarly, the MDT of the parent strain LaSota was greater than 120 h, and the ICPI value was 0.00. Therefore, the rLS-tFib2-C strain maintains the attenuated characteristics of the parent LaSota strain.

What is claimed is:

1. A heat-resistant recombinant Newcastle Disease Virus vaccine strain rLS-tFib2-C expressing truncated Fiber 2 protein of fowl adenovirus serotype 4 which has been preserved at the China Center for Type Culture Collection, Wuhan University, Wuhan, China with the preservation number of CCTCC No. V202042, the rLS-tFib2-C comprising a parent strain NDV LaSota with an HN gene replaced with an HN gene of the NDV TS09-C strain and comprising an inserted 961-1440 bp region of a Fiber2 gene of a Fowl Adenovirus serotype 4 between P and M genes of the parent strain in the form of a separate coding frame.

2. The heat-resistant recombinant Newcastle Disease Virus strain rLS-tFib2-C according to claim 1, wherein the rLS-tFib2-C vaccine strain is obtained by using a NDV LaSota strain as a parent strain, and replacing an HN gene of the LaSota strain with an HN gene of the NDV TS09-C strain, and then inserting a 961-1440 bp region of truncated Fiber2 gene of the Fowl Adenovirus serotype 4 between P and M genes of the parent strain in the form of a separate coding frame.

3. The heat-resistant recombinant Newcastle Disease Virus vaccine strain rLS-tFib2-C according to claim 1, wherein the HN protein gene of the NDV LaSota strain has the sequence of SEQ ID NO: 1.

4. The heat-resistant recombinant Newcastle Disease Virus vaccine strain rLS-tFib2-C according to claim 1, wherein the 961-1440 bp region of truncated Fiber2 gene of the Fowl Adenovirus serotype 4 has the sequence of SEQ ID NO: 2.

* * * * *

SEQUENCE LISTING

```
<160> NUMBER OF SEQ ID NOS: 10

<210> SEQ ID NO 1
<211> LENGTH: 1851
<212> TYPE: DNA
<213> ORGANISM: Newcastle Disease Virus

<400> SEQUENCE: 1
atggaccgcg cagttagcca agttgcgcta gagaatgatg aaagagaggc aaagaataca      60
tggcgcttgg tattccggat cgcaatccta ctctcaacgg tggtgacctt agccatctct     120
gcagccgccc ttgcatatag catggaggcc agcacaccta gcgatcttgt aggcataccg     180
actgcgatct ctagagcaga ggaaaagatt acatctgcac tcggttccaa tcaagatgta     240
gtagatagga tatataagca ggtggccctc gaatctccac tggcattgct aaacaccgaa     300
tctacaatta tgaacgcaat aacgtctctc tcttatcaaa tcagtggggc cgcaagtagc     360
agcggatgtg gagcacccat tcatgatcca gattatattg gaggaatagg taaagaactt     420
attgtagatg atgctagcga cgtcacatca tactatccct ctgcgttcca agaacacctg     480
aactttatcc cggcgcctac tacaggatca ggttgcactc ggatgccctc atttgacatg     540
agcgctaccc actactgtta tactcacaat gtgatattat ctggctgcag agatcactcg     600
cactcacatc aatatttagc acttggtgtg cttcggacat ctgcaacagg gagggtattc     660 tttttccactc tgcgttccat caatctggat gacacccaaa atcggaagtc ttgcagtgtg     720
agtgcaaccc ccttgggttg tgatatgctg tgctctaaag tcacagagac tgaagaagag     780
gattataact cagctatccc cacgtcgatg gtacatggaa ggttagggtt cgacggccaa     840
taccacgaga aggacctaga tgtcacaaca ctattcgagg actgggtggc aaactaccca     900
```

```
ggagtaggag gcgggtcttt tattgacaac cgcgtatggt tcccagttta cggagggcta      960
aaacccaatt cgcccagtga caccgcacaa gaagggaaat atgtaatata caagcgatac     1020
aatgacacat gtccagatga gcaagattat cagattcaaa tggctaagtc ttcatataag     1080
cctgggcggt ttggagggaa acgcgtacag caggccgtct tatctatcaa agtgtcaaca     1140
tccttgggcg aggacccggt gctgactgta ccgcccaaca cagtaacact catggggcc      1200 gaaggcagag ttctcacagt agggacatct catttccttt atcagcgagg gtcatcatac     1260
ttctcccctg ccctactata tcctatgata gtcagcaaca aaacagccac tcttcatagt     1320
ccttatacat tcaatgcctt cactcgacca ggtagtgtcc cttgccaggc ttcagcaaga     1380
tgccctaact catgtgttac cggagtctat actgatccat atcccttggt cttctatagg     1440
aaccacacct tgcgagggt attcgggacg atgcttgatg ataaacaagc aagactcaac     1500
cctgtatctg cagtatttga cagcatatcc cgcagtcgca taacccgggt gagttcaagc     1560
agcaccaagg cagcatacac aacatcaaca tgttttaaag ttgtaaagac caataaaacc     1620
tattgtctca gcattgccga aatatccaat accctcttcg gggaattcag aatcgtccct     1680
ttactagttg agattctcaa ggatgatggg gttagagaag ccaggtctag ccggttgagt     1740
caactgcgag agggttggaa agatgacatt gtatcaccta tcttttgcga cgccaagaat     1800
caaactgaat accggcacga gctcgagtcc tacgctgcca gttggccata a              1851

<210> SEQ ID NO 2
<211> LENGTH: 480
<212> TYPE: DNA
<213> ORGANISM: Fowl Adenovirus Serotype 4

<400> SEQUENCE: 2
gggctccttg ttacctccct ctacttgaaa ttggacagcg ccaccatggg gaatcgccct       60
ggggacctca actccgccaa tgccaaatgg ttcacctttt gggtgtccgc ctatctccag      120
caatgcaacc cctccgggat tcaagcggga acgtcagcc cctccaccgc caccctcacg      180
gactttgaac ccatggccaa taggagcgtg accagcccat ggacgtactc ggccaatgga      240
tactatgaac catccatcgg ggaattccaa gtgttcagcc cggtggtaac aggtgcctgg      300
aacccgggaa acatagggat ccgcgtcctc cccgtgccgg tttcggcctc cggagagcga      360
tacacccttc tatgctatag tctgcagtgc acgaacgcga gcattttttaa tccaaacaac      420 agcggaacca tgatcgtggg acccgtgctc tacagctgtc cagcggcctc cctcccgtaa      480

<210> SEQ ID NO 3
<211> LENGTH: 31
<212> TYPE: DNA
<213> ORGANISM: Artificial sequence
<220> FEATURE:
<223> OTHER INFORMATION: sythetic construct

<400> SEQUENCE: 3
ttgagtcaat tataaaggag ttggaaagat g                                      31

<210> SEQ ID NO 4
<211> LENGTH: 25
<212> TYPE: DNA
<213> ORGANISM: Artificial sequence
<220> FEATURE:
<223> OTHER INFORMATION: sythetic construct

<400> SEQUENCE: 4
gattgaggac agttgtcggt gaagc                                             25
```

```
<210> SEQ ID NO 5
<211> LENGTH: 35
<212> TYPE: DNA
<213> ORGANISM: Artificial sequence
<220> FEATURE:
<223> OTHER INFORMATION: sythetic construct

<400> SEQUENCE: 5
caacagtcct caatcatgga ccgcgcagtt agcca                                35

<210> SEQ ID NO 6
<211> LENGTH: 39
<212> TYPE: DNA
<213> ORGANISM: Artificial sequence
<220> FEATURE:
<223> OTHER INFORMATION: sythetic construct

<400> SEQUENCE: 6
ctttataatt gactcaatta tggccaactg gcagcgtag                            39

<210> SEQ ID NO 7
<211> LENGTH: 20
<212> TYPE: DNA
<213> ORGANISM: Artificial sequence
<220> FEATURE:
<223> OTHER INFORMATION: sythetic construct

<400> SEQUENCE: 7
ttggagtgcc ccaattgtgc                                                 20

<210> SEQ ID NO 8
<211> LENGTH: 33
<212> TYPE: DNA
<213> ORGANISM: Artificial sequence
<220> FEATURE:
<223> OTHER INFORMATION: sythetic construct

<400> SEQUENCE: 8
tcttaaatgt agctagatta attacggtta cgc                                  33

<210> SEQ ID NO 9
<211> LENGTH: 67
<212> TYPE: DNA
<213> ORGANISM: Artificial sequence
<220> FEATURE:
<223> OTHER INFORMATION: sythetic construct

<400> SEQUENCE: 9
ctagctacat ttaagattag aaaaaatacg ggtagaagcc accatggggc tccttgttac     60
ctcccctc                                                              67

<210> SEQ ID NO 10
<211> LENGTH: 57
<212> TYPE: DNA
<213> ORGANISM: Artificial sequence
<220> FEATURE:
<223> OTHER INFORMATION: sythetic construct

<400> SEQUENCE: 10
attggggcac tccaattcta cccgtgtttt ttctaattat tacgggaggg aggccgc        57
```